United States Patent
Mozeleski et al.

(10) Patent No.: US 6,677,481 B2
(45) Date of Patent: Jan. 13, 2004

(54) CRACKING OF NEO-$C_9$ AND NEO-$C_{13}$ CARBOXYLIC ACIDS TO EITHER PIVALIC ACID OR METHYL PIVALATE

(75) Inventors: Edmund J. Mozeleski, Califon, NJ (US); Richard H. Schlosberg, Bridgewater, NJ (US); Dennis J. Davoren, Baton Rouge, LA (US); Carl Robert Beck, Greenwell, LA (US); Linda J. Broadbelt, Glenview, IL (US); Ned C. Haubein, Evanston, IL (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 70 days.

(21) Appl. No.: 09/901,238

(22) Filed: Jul. 9, 2001

(65) Prior Publication Data
US 2003/0028049 A1 Feb. 6, 2003

(51) Int. Cl.[7] ............................................. C07C 51/14
(52) U.S. Cl. ............................................... 562/521
(58) Field of Search ................................ 562/517, 521

(56) References Cited

U.S. PATENT DOCUMENTS

| | | | |
|---|---|---|---|
| 1,516,720 A | 11/1924 | Ellis | |
| 1,529,946 A | 3/1925 | Dubin et al. | |
| 2,531,363 A | 11/1950 | Pelton et al. | 260/540 |
| 2,777,865 A | 1/1957 | Logan | 260/413 |
| 3,527,779 A | 9/1970 | Paulis et al. | 260/413 |
| 3,665,034 A | 5/1972 | Komatsu et al. | 260/533 A |
| 3,865,855 A | 2/1975 | Linn et al. | 260/413 |
| 4,536,594 A | 8/1985 | Deschamps et al. | 562/400 |
| 4,663,479 A | 5/1987 | Velenyi et al. | 562/525 |
| 5,227,521 A | 7/1993 | Richard et al. | 562/521 |
| 5,241,112 A | 8/1993 | Sanderson et al. | 562/521 |
| 5,990,351 A | 11/1999 | Cabre et al. | 562/606 |

OTHER PUBLICATIONS

"Carboxylation of Isobutylene with Carbon Monoxide and Water in the Presence of $BF_3$–$2H_2O$ Catalyst", Norihiko Yoneda et al., Japanese Chemical Society Journal, (8), pp. 1475–1480, (1972).

"Carboxylation of Isobutylene and Related Olefins with Carbon Monoxide and Water in the Presence of $BF_3$–$H_2O$ Complex Catalysts", Norihiko Yoneda et al., Bulletin of The Japan Institute, vol. 14, No. 2, pp. 178–186, (Nov., 1972).

Primary Examiner—Mukund J. Shah
Assistant Examiner—Zachary C. Tucker
(74) Attorney, Agent, or Firm—Linda A. Kubena (57) ABSTRACT

A method for production of pivalic acid comprising the steps of: (a) reacting isobutylene, carbon monoxide, and a first catalyst to produce a reaction mixture; (b) contacting the reaction mixture with water, thereby producing a crude acid product having pivalic acid and oligomeric neo-carboxylic acid; (c) then separating the pivalic acid and the oligomeric neo-carboxylic acid from the crude acid product; (d) then reacting the oligomeric neo-carboxylic acid with a source of carbon monoxide at a temperature of less than 200° C. in the presence of a second catalyst to produce a $C_5$ carbocation product, wherein the first and second catalyst are either the same or different; and (e) reacting the $C_5$ carbocation product with water; thereby producing pivalic acid having an overall yield of at least 80 wt. %.

18 Claims, 5 Drawing Sheets

CRACKING OF NEO-$C_9$ AND NEO-$C_{13}$ CARBOXYLIC ACIDS TO EITHER PIVALIC ACID OR METHYL PIVALATE

BACKGROUND OF THE INVENTION

1. Field of the Invention

The present invention relates to production of pivalic acid and methyl pivalate. More particularly, the present invention is directed to a method for producing pivalic acid and methyl pivalate by cracking $C_9$ and $C_{13}$ carboxylic acids to pivalic acid or methyl pivalate.

2. Description of Related Art

Pivalic acid (2,2-dimethylpropanoic acid) is widely used as a starting material for various agrochemical, pharmaceuticals, aroma chemicals, specialty chemicals, and polymer additives.

Current processes produce pivalic acid in yields of approximately 74% pivalic acid or less. The by-products are mainly higher molecular weight oligomeric carboxylic acids with carbon numbers of $C_9$ and $C_{13}$ and higher. The carboxylic acids are typically separated by phase separation from the boron trifluoride dihydrate catalyst and further purified by distillation resulting in the following components:

In the neo acid process, a hydrocarbon feed or a compound capable of forming a reactive hydrocarbon intermediate, carbon monoxide and recycled catalyst are fed to a continuous process to manufacture an α,α-branched quaternary carboxylic acid. The term "hydrocarbon feed" as used herein includes, but is not limited to, olefins, alcohols and ethers which are capable of forming a reactive hydrocarbon intermediate. The catalyst is a strong acid, typically hydrates of boron trifluoride and occasionally containing a co-catalyst such as phosphoric acid. Other possible catalysts include Lewis acids, zeolite or modified zeolite catalysts, hydrofluoric acid, sulfuric acid, and solid acid catalysts.

One such conventional process for the preparation of pivalic acid is set forth in U.S. Pat. No. 5,241,112 (Sanderson et al.), which is incorporated herein by reference. Sanderson et al. specifically relate to a process for the production of pivalic acid from branched olefins, particularly isobutene and carbon monoxide using a solid acid catalyst and, optionally, with minor amounts of a Lewis acid, such as boron trifluoride. The solid acid catalyst is typically a compound comprising sulfonic acid and phosphonic acid groups, where the phosphonic acid groups are covalently bonded to a polymeric chain.

Figure 1:
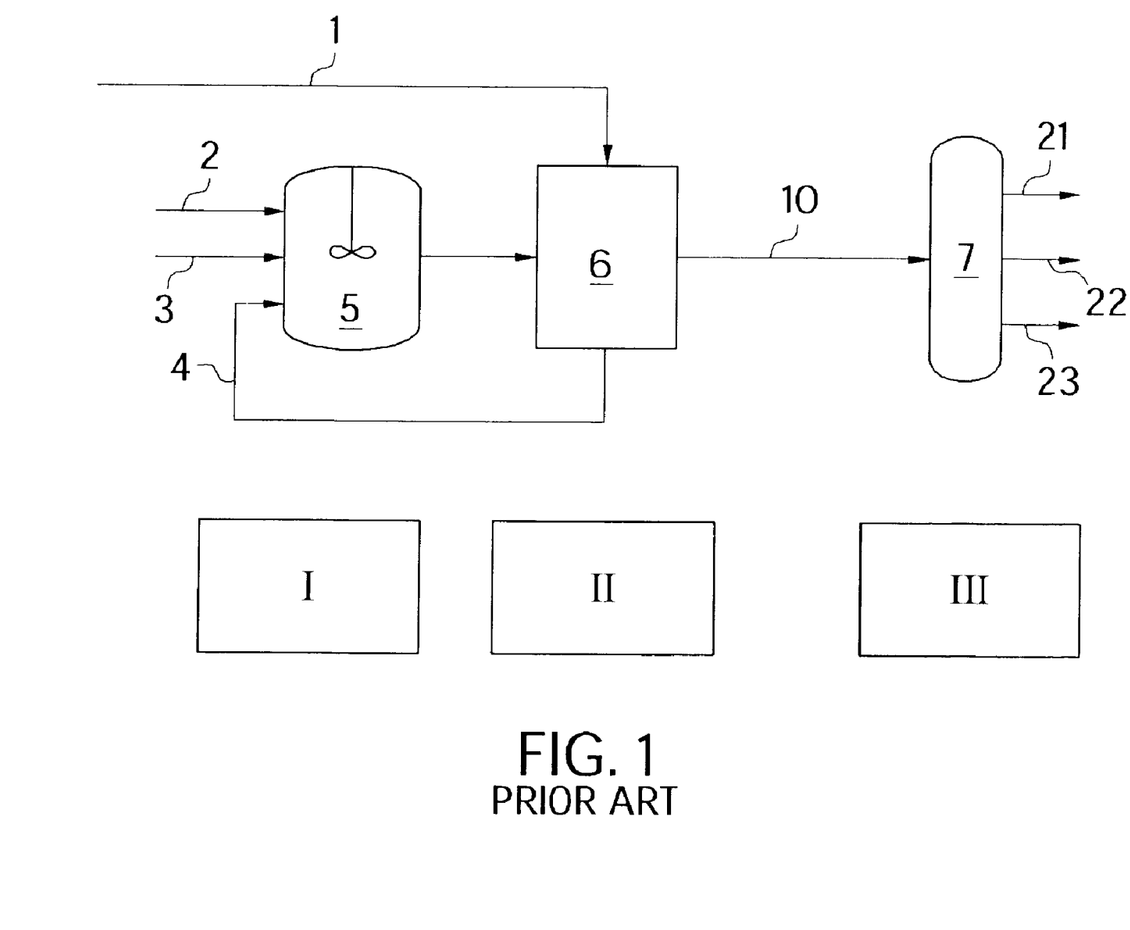
FIG. 1 is a prior art schematic of the process for production of pivalic acid.

An example of a typical process for manufacturing pivalic acid is shown in FIG. 1. In reaction step I, conduits 2 and 3 continuously feed isobutylene and carbon monoxide, respectively, to a back mixed, stirred tank reactor 5 having a boron trifluoride dihydrate catalyst disposed therein. Step II, the catalyst recovery step, occurs when the reactor effluent is contacted with water 1 in separator 6 to provide crude pivalic acid, and to extract the boron trifluoride dihydrate catalyst, which is recycled back via conduit 4 to reactor 5. The crude pivalic acid product is fed to distillation tower via conduit 10, where it is then purified in distillation step III. Pivalic acid is separated from the $C_9$ and $C_{13}$ acids and oligomeric acids with more than 13 carbons. The pivalic acid is removed from tower 7 via conduit 21 and the oligomeric acids are removed as bottoms via conduit 23. $C_9$ and $C_9$ and $C_{13}$ acids are separated from pivalic acid and oligomeric acids with more than 13 carbons via a conduit 22. Depending on a variety of process conditions, significant amounts of $C_8$ and $C_{12}$ oligomers are also formed from the oligomerization of the feed olefin before carboxylation occurs. Increasing the reaction temperature reduces these unwanted by-products, but also undesirably increases the rate of corrosion. Since these by-product acids occur with carbon numbers that differ by four, they are easily separated by distillation. However, under low temperature conditions, which is preferred to minimize corrosion, selectivity to the desired pivalic acid product is adversely affected.

The present invention addresses these problems and is directed to a novel and unique process for increasing the yield by back cracking oligomeric carboxylic acids to pivalic acid or methyl pivalate. The present invention is able to increase the yield by separating the $C_9$ and $C_{13}$ acids from the crude pivalic acid product and either recycling them back to the pivalic acid reactor or by post-treatment. These $C_9$ and $C_{13}$ acids break down to form pivalic acid ($C_5$), thus increasing the effective selectivity. Using the novel approach according to the present invention, lower temperatures can be used to achieve selectivity to pivalic acid, which was heretofore only attainable at higher, more corrosive temperatures. An additional benefit of the process according to the present invention is that the recycled $C_9$ and $C_{13}$ acid stream acts as a diluent in the feed isobutylene, which further inhibits oligomerization of the isobutylene.

SUMMARY OF THE INVENTION

A method for the production of pivalic acid which comprises: (a) reacting an oligomeric neo carboxylic acid with a source of carbon monoxide at a temperature of less than about 200° C, preferably between about 90° C. to about 200° C. more preferably between about 90° C. to about 150° C. in the presence of a catalyst to produce a $C_5$ carbocation product; and (b) reacting the $C_5$ carbocation product with water; thereby producing pivalic acid. Preferably, step (a) comprises the steps of: (i) decarbonylating the neo-carboxylic acid to form a $C_{n-1}$ carbocation, wherein n is equal to the number of carbon atoms present in the neo-carboxylic acid; (ii) cracking the $C_{n-1}$ carbocation to form a $C_4$ carbocation; and (iii) reacting the $C_4$ carbocation with the source of carbon monoxide to form the $C_5$ carbocation product. The partial pressure of carbon monoxide is preferably in the amount from about 50 psig to about 2000 psig, more preferably about 500 psig to about 1500 psig.

Another embodiment according to the present invention is a method for production of alkyl pivalate comprising: (a)

reacting an oligomeric neo-carboxylic acid with a source of carbon monoxide at a temperature of less than about 200° C. preferably between about 100° C. to about 160° C. in the presence of a catalyst to produce a $C_5$ carbocation product; and (b) reacting the $C_5$ carbocation product with alcohol; thereby producing the alkyl pivalate.

A further embodiment according to the present invention comprises a method of controlling the oligomerization of pivalic acid comprising: (a) producing pivalic acid, wherein a by-product of producing pivalic acid is an oligomeric neo-carboxylic acid; (b) separating the by-product oligomeric neo-carboxylic acid from the pivalic acid; (c) reacting the oligomeric neo-carboxylic acid with a source of carbon monoxide at a temperature of less than about 200° C. in the presence of a catalyst to produce a $C_5$ carbocation product; and (d) reacting the $C_5$ carbocation product with water; thereby producing pivalic acid having an overall yield of at least 80 wt. %.

Still a further embodiment according to the present invention comprises a method for production of pivalic acid comprising: (a) reacting isobutylene, carbon monoxide, and a catalyst to produce a reaction mixture; (b) contacting the reaction mixture with water to regenerate catalyst and/or to produce a crude acid product having pivalic acid and oligomeric neo-carboxylic acid; (c) separating the pivalic acid from the oligomeric neo-carboxylic acid; (d) reacting the oligomeric neo-carboxylic acid with a source of carbon monoxide at a temperature of less than 200° C. in the presence of a catalyst to produce a $C_5$ carbocation product; and (e) the $C_5$ carbocation product reacting with water; thereby producing pivalic acid having an overall yield of at least 80 wt. %.

According to still another embodiment of the present invention, a method for production of alkyl pivalate comprising: (a) reacting isobutylene, carbon monoxide, and a first catalyst to produce a reaction mixture, (b) contacting the reaction mixture with an alcohol to regenerate the first catalyst and to produce a crude product having alkyl pivalate and an oligomeric neo-carboxylic acid; (c) separating alkyl pivalate from the oligomeric neo-carboxylic acid; (d) reacting the oligomeric neo-carboxylic acid with carbon monoxide at a temperature of less than about 180° C. in the presence of a second catalyst to produce a $C_5$ carbocation product; and (e) reacting the $C_5$ carbocation product with alcohol; thereby producing methyl pivalate.

DETAILED DESCRIPTION OF THE INVENTION

The present invention provides an efficient method for converting larger molecular weight acids to lower molecular weight acids. The process cracks the larger molecular weight acid at temperatures that are low enough to avoid decomposition of the acid, and avoid corrosion, while still high enough to efficiently crack the acid. The process is both simple and adaptable to existing systems for production of acids, such as pivalic acid. The catalyst for cracking can be the same catalyst used in the production of the pivalic acid reaction, such as hydrates of boron trifluoride and optionally containing a co-catalyst, such as phosphoric acid or Ag/Cu. Other possible catalysts include Lewis acids, zeolite or modified zeolite catalysts, hydrofluoric acid, sulfuric acid, and solid acid catalysts. The strong Lewis acids may include, but are not limited to, $AlCl_3$, $AlBr_3$, $SbF_5$, $TaF_5$, etc.

Figure 2:
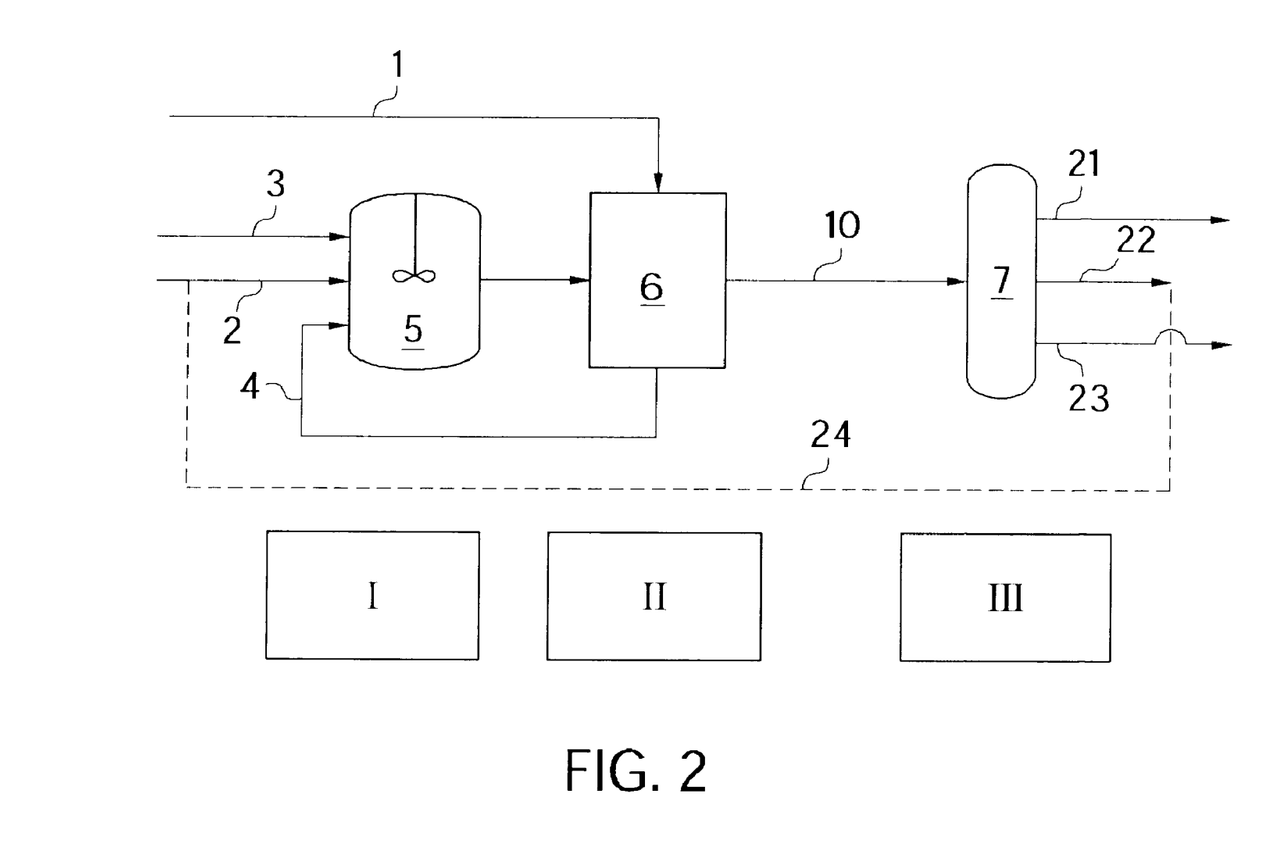
FIG. 2 is a schematic of the process detailed in the present invention.

FIG. 2 depicts the process scheme according to the present invention, wherein step I involves conduits 2 and 3 continuously feeding isobutylene and carbon monoxide, respectively, to a back mixed, stirred tank reactor 5 having a boron trifluoride dihydrate catalyst disposed therein. Step II, the catalyst recovery step, occurs when the reactor effluent is contacted with water 1 in separator 6 to provide crude pivalic acid, and to extract the boron trifluoride dihydrate catalyst, which is recycled back via conduit 4 to reactor 5. The crude pivalic acid product is fed to distillation tower via conduit 10, where it is then purified in distillation step III. Pivalic acid is separated from the $C_9$ and $C_{13}$ acids and oligomeric acids with more than 13 carbons. The pivalic acid is removed from tower 7 via conduit 21 and the oligomeric acids are removed as bottoms via conduit 23. $C_9$ and $C_{13}$ acids are separated from pivalic acid and oligomeric acids with more than 13 carbons via a conduit 22. The separated $C_9$ and $C_{13}$ carboxylic acids are removed from tower 7 as a side stream 22 and recycled to reactor 5 via conduits 24 and 2 wherein they are cracked back to pivalic acid or methyl pivalate, then separated by phase separation from other components and further purified by distillation. As shown in FIG. 2, the by-product $C_9$ and $C_{13}$ acids are separated from the crude product by distillation III and then recycled back to the reactor via conduit 22 thereby approaching complete recycling of the $C_9$ and $C_{13}$ acids to desired products. These larger molecular weight acids are treated in such a way as to form pivalic acid ($C_5$), thus increasing the effective selectivity. With this approach, lower temperatures are used to achieve selectivity to pivalic acid, which was heretofore only attainable at higher, more corrosive temperatures. An additional benefit of this process configuration is that the recycled $C_9$ and/or $C_{13}$ acid stream is a diluent in the feed isobutylene, which further inhibits oligomerization of the isobutylene. By this process, the overall yield of pivalic acid is higher than achieved by previous processes. Therefore, the present process provides an inexpensive and commercially adaptable answer for obtaining higher yield of pivalic acid or methyl pivalate.

Figure 5:
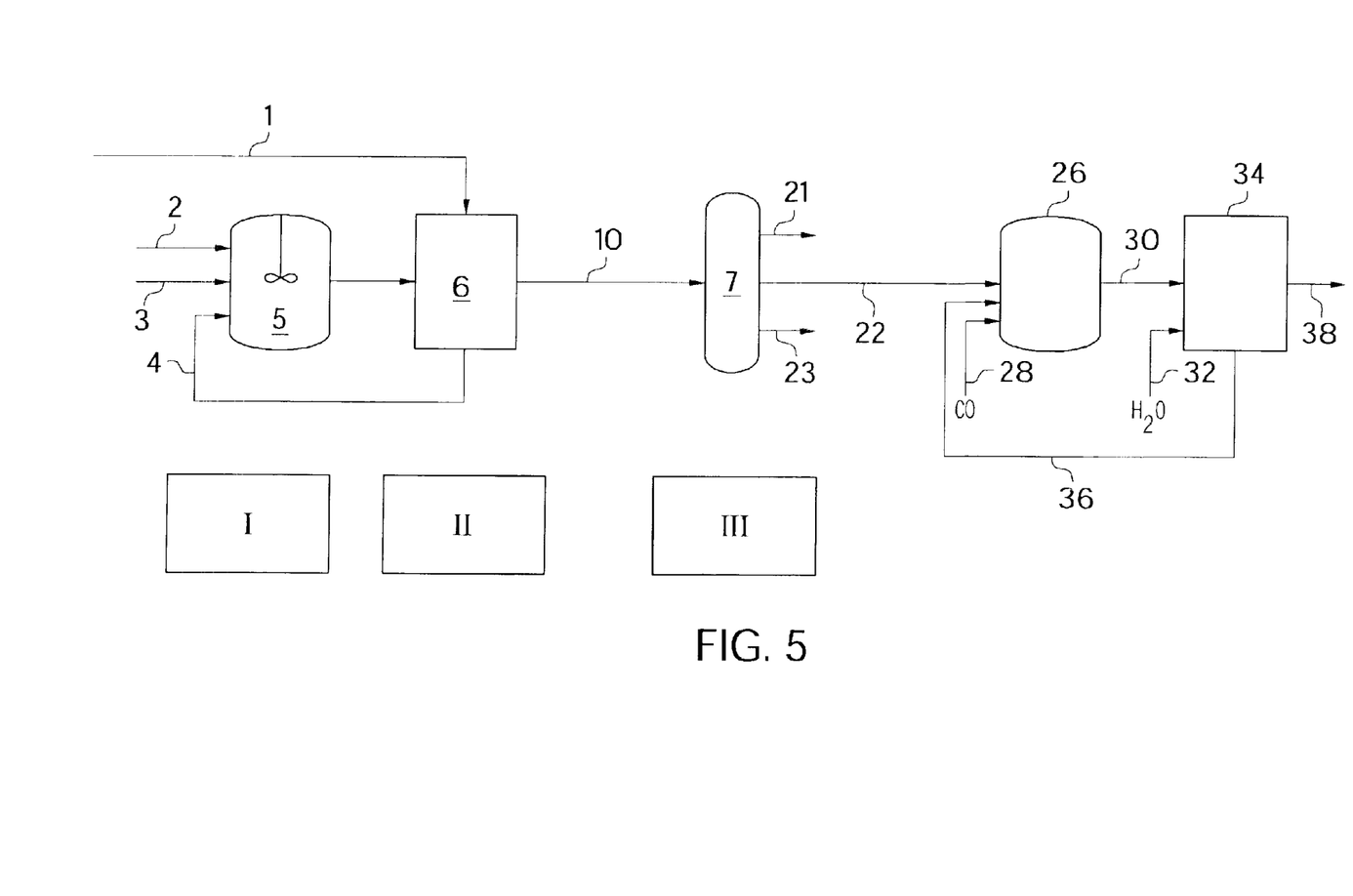
FIG. 5 is a schematic representation of another embodiment according to the present invention, wherein the $C_9$ and $C_{13}$ carboxylic acids are sent to a cracking vessel for conversion back to pivalic acid or methyl pivalate.

FIG. 5 depicts another method according to the present invention, wherein $C_9$ and/or $C_{13}$ carboxylic acids are taken from distillation tower 7 via conduit 22 and reacted with a source of carbon monoxide (e.g., either carbon monoxide or formic acid) supplied via conduit 28 in cracking vessel 26 at a temperature of less than about 200° C. preferably about 90° C. to about 200° C. and more preferably about 90° C. to about 150° C., in the presence of a catalyst to produce a $C_5$ carbocation product; withdrawing $C_5$ carbocation product from vessel 26 via conduit 30 and reacting the $C_5$ carbocation product with water supplied via conduit 32 to reactor 34; thereby producing pivalic acid which is removed via conduit 38. The catalyst is removed via conduit 36 and returned to vessel 26.

The aforementioned step of reacting the oligomeric carboxylic acid with a source of carbon monoxide in cracking vessel 26 to produce a $C_5$ carbocation product preferably comprises the following in situ steps: (i) decarbonylating the neo-carboxylic acid to form a $C_{n-1}$ carbocation, wherein n is equal to the number of carbon atoms present in the neo-carboxylic acid; (ii) cracking the $C_{n-1}$ carbocation to form a $C_4$ carbocation; and (iii) reacting the $C_4$ carbocation with the source of carbon monoxide to form the $C_5$ carbocation product. These steps are conducted at a partial pressure that in the amount from about 50 psig to about 2000 psig, preferably about 500 psig to about 1500 psig. The molar ratio of catalyst to oligomeric neo-carboxylic acid is at least 1:1 and the molar ratio of water to the oligomeric neo-carboxylic acid is at least about 1:1. The catalyst is preferably at least one selected from the group consisting of: hydrates of boron trifluoride, hydrofluoric acid, sulfuric acid, solid acid catalysts, and mixtures thereof. The preferred catalyst is boron trifluoride dihydrate, which can be regenerated via the water in reactor 34 before being recycled to vessel 26.

Alternatively, the process of FIG. 5 can be used to produce alkyl pivalate as follows: reacting an oligomeric neo-carboxylic acid (e.g., $C_9$ and/or $C_{13}$) with a source of carbon monoxide at a temperature of less than about 180° C., preferably 120° C. to about 150° C., in the presence of a catalyst to produce a $C_5$ carbocation product; and reacting the $C_5$ carbocation product with alcohol; thereby producing the alkyl pivalate.

The catalyst is at least one selected from the group consisting of: alcohols of boron trifluoride, including $BF_3.XCH_3OH$, $BF_3.XC_2H_5OH$, $BF_3.XC_3H_8OH$, and mixtures thereof, preferably $BF_3.XCH_3OH$ where X is between about 2.0 to 2.5, and most preferably boron trifluoride dimethanol (i.e., $BF_3.XCH_3OH$ where X is 2.0). The alcohol is preferably methanol, which may also be used to regenerate the boron trifluoride dimethanol.

The following Experiments are presented to illustrate the invention, but the invention is not to be considered as limited thereto.

EXPERIMENT 1

The catalyst was first prepared in the 150 cc Hastelloy C autoclave as follows: water (30 g, 1.66 mol) was added with nitrogen followed by boron trifluoride (56.7 g, 0.833 mol) from a pressure/volume/temperature (PVT) vessel. Next $C_9$–$C_{13}$ carboxylic acids (23.75 g) were added with nitrogen pressure to the boron trifluoride dihydrate. The nitrogen overpressure was released and carbon monoxide (CO) was added to 1025 psi. The reaction mixture was then heated to 100° C. At 100° C., the CO pressure was adjusted to 1200 psi. The reaction mixture was heated for 2 hours then gas chromatography (gc) sampled. The reaction mixture was cooled under CO pressure and the temperature was maintained for an additional 4 hours for a total of 6 hours. The following table indicates conversion of the $C_9$–$C_{13}$ carboxylic acids to pivalic acid after 2, 4, and 6 hours of heating respectively:

| Run Time (minutes) | methyl pivalate (wt. %) | pivalic acid (wt. %) | 2-methyl butanoic acid (wt. %) | $C_9$-neo acids (wt. %) | $C_{13}$-neo acids (wt. %) |
| --- | --- | --- | --- | --- | --- |
| 0 | 0 | 0 | 0 | 86.44 | 12.10 |
| 120 | 1.51 | 36.22 | 1.04 | 55.62 | 5.60 |
| 240 | 2.34 | 75.29 | 1.93 | 17.73 | 2.72 |
| 360 | 3.14 | 80.95 | 2.27 | 12.51 | 1.13 |

After heating 6 hours at 100° C. under 1200 psi CO pressure, the contents of the autoclave were cooled to room temperature. At room temperature, the CO overpressure was released then the reaction mixture was drained from the autoclave into a sample bottle. Two phases were obtained, i.e., a clear light yellow liquid boron trifluoride dihydrate catalyst phase and a hazy orange upper product phase. The upper product phase contained mainly pivalic acid with a small amount of 2-methylbutanoic acid and unreacted neo-$C_9$ and neo-$C_{13}$ carboxylic acids.

EXPERIMENT 2

The second experiment was similar to the first experiment, except no gc samples were taken and the catalyst solution plus starting $C_9$–$C_{13}$ neoacids were allowed to stand in the autoclave at room temperature overnight under CO pressure prior to heating. Also, the same quantities of water and boron trifluoride dihydrate were added with one exception, i.e., 20.12 g of neo-$C_9$–$C_{13}$ acids were also added. The reaction mixture was then heated to 100° C. and the run temperature was maintained at 100° C. for 3 hours under 1200 psi CO pressure. The temperature of the reaction mixture was then lowered to room temperature and was left to stand overnight. The following day, the reaction mixture was heated back to 100° C. under CO pressure and the temperature was maintained for an additional 3 hours for a total of 6 hours. The reaction mixture was then cooled to room temperature and at room temperature the CO overpressure was released. The reaction mixture was drained from the autoclave into a sample bottle. The lower catalyst phase was clear yellow liquid weighing 67.80 g which corresponds to 78.2 wt. % of the starting boron trifluoride dihydrate and the upper pivalic acid phase (i.e., clear orange liquid) weighed 29.31 g which corresponds to 145.7 wt. % of the starting $C_{9-13}$ neoacids. Gas chromatography analysis of the upper carboxylic acid phase revealed methyl pivalate (0.86 wt. %), pivalic acid (82.6 wt/ %), 2-methylbutanoic acid (2.4 wt. %), neo- $C_9$ carboxylic acids (11.0 wt. %) and neo- $C_{13}$ carboxylic acids (3.1 wt. %). The upper product phase was injected into the gc as such with no added water to the acid phase.

EXPERIMENT 3

The third experiment was similar to the first experiment, except the run temperature was lowered to 80° C. Also, the 6 hour heating period was accomplished in one day with gc sampling after 2, 4, and 6 hours. The following table summarizes the gc results in weight percent:

| Run Time (minutes) | methyl pivalate | pivalic acid | C5 acid | $C_9$ acid | $C_{13}$ acid |
|---|---|---|---|---|---|
| 120 | 0.04 | 1.26 | 0.31 | 88.35 | 10.04 |
| 240 | 0.13 | 3.71 | 0.04 | 86.09 | 10.02 |
| 360 | 0.11 | 5.65 | 0.30 | 83.82 | 10.12 |

Figure 3:
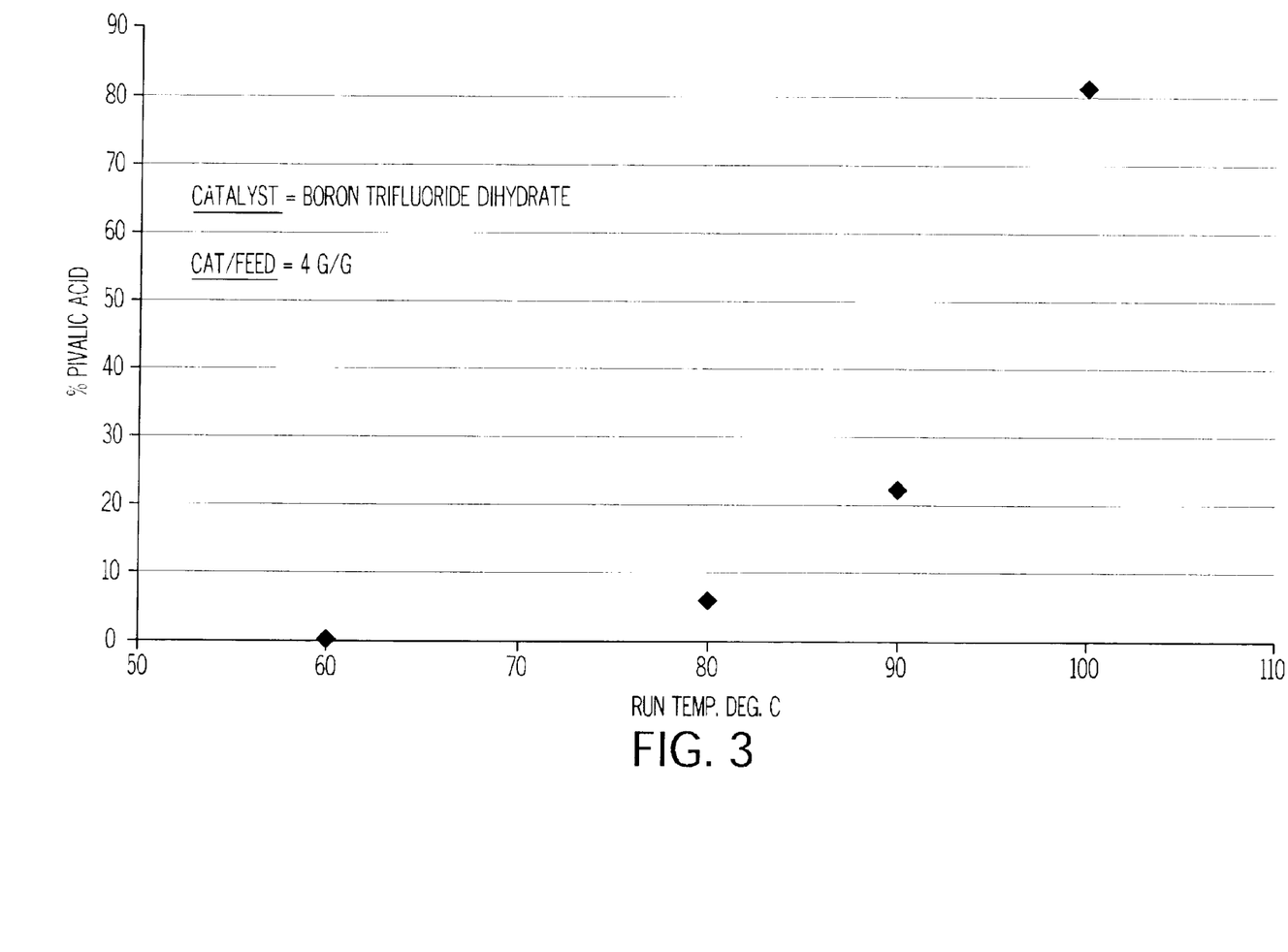
FIG. 3 is a graph depicting percent pivalic acid versus reaction temperature according to the present invention.
Figure 4:
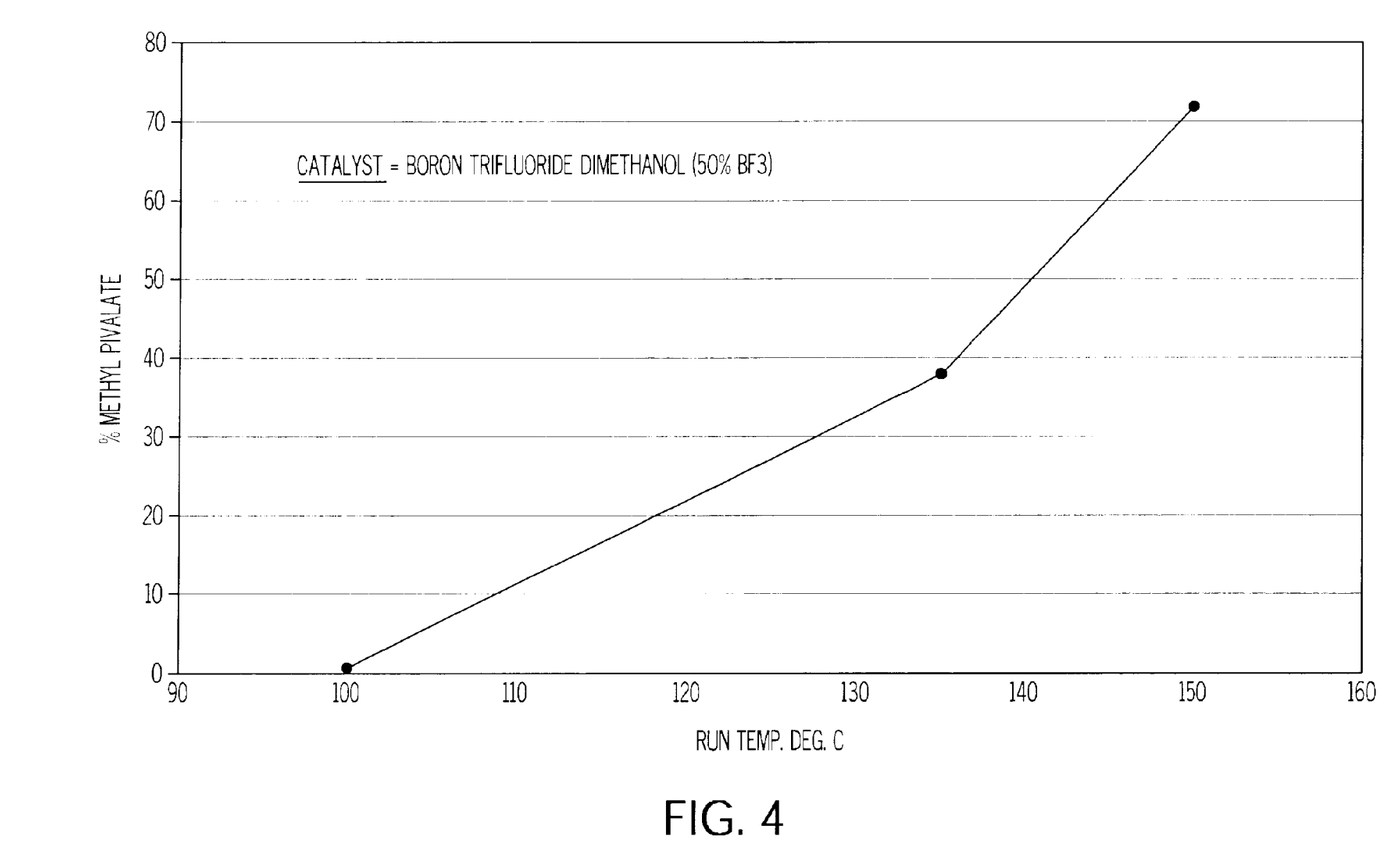
FIG. 4 is a graph depicting percent yield of methyl pivalate using boron trifluoride dimethanol versus reactor temperature according to the present invention.

FIG. 3 shows the temperature requirements to obtain high $C_{9-13}$ neoacid retro-conversion to pivalic acid by plotting the percent pivalic acid in the upper phase analysis. For experiments 1, 2, and 3, boron trifluoride dihydrate catalyst was used with the best results at 100° C.

In the next series of experiments, i.e., Experiments 4–6, boron trifluoride dimethanol was used resulting in the production of methyl pivalate in commercially acceptable yields.

EXPERIMENT 4

The boron trifluoride concentration in the catalyst was 50 weight % with the balance $BF_3.XCH_3OH$ catalyst, wherein X is 2.12. The $C_9$ and $C_{13}$ carboxylic. acids were not miscible with the boron trifluoride dimethanol at room temperature. The mixture was transferred to a 150 cc Hastelloy C autoclave with nitrogen pressure. The nitrogen overpressure was released and the autoclave was pressured to about 1000 psi with carbon monoxide. The reaction mixture was then heated to 135° C. under CO pressure at temperature in 88 minutes, the pressure was adjusted to 1200 psi from 1125 psi. The temperature and pressure were maintained for 4.5 hours. At the completion of the heating period, the contents were cooled to room temperature. The CO overpressure was released and the contents were drained into a sample bottle. A clear homogeneous clear red liquid resulted. The reaction mixture was diluted with excess methanol (2 parts methanol to 1 part reaction mixture) and sampled for gc analysis as such. The gc results revealed essentially complete conversion of the carboxylic acids to the .methyl esters and 38 wt. % methyl pivalate. No internal standard was used in all of the experiments. The areas were adjusted for response factors and the resulting percentages were normalized to 100%.

EXPERIMENT 5

This experiment was conducted at 100° C. for 6 hours. The same procedure was followed as Experiment 4. The resulting methyl pivalate make was only 0.5 wt. % indicating 100° C. was insufficient. The $C_9$ and $C_{13}$ carboxylic acids were converted to the corresponding methyl esters.

EXPERIMENT 6

This experiment was the same as experiment 5 except at a run temperature of 150° C., significant methyl pivalate (72 wt. %) was revealed by gc and $C_9$ acid methyl esters (26 wt. %) and $C_{13}$ acid methyl esters (2.5 wt. %).

FIG. 3 demonstrates the temperature requirements to obtain high yields and selectivities to methyl pivalate from the $C_9$ and $C_{13}$ oligomeric carboxylic acids as performed in Experiments 4, 5, and 6. The best results were shown at 150° C. when boron trifluoride dimethanol was used.

The reference in the Japanese Chemical Society Journal, 1475–80 (1972), reveals only a 6.0 wt. % yield of pivalic acid at 100° C. and 710 psi in 4 hours with a $C_9$ carboxylic acid feed and cyclohexane solvent versus our results in 4 hours at a100°C./1200 psi with no solvent (75 wt. %). Also, this reference indicates that temperatures greater than or equal to 120° C. are required. In the present invention, high selectivity was determined at 1.00° C. And the reference in the Japanese Chernical Society Journal did not disclose any conversion of neo-carboxylic acids to methyl pivalate.

The cracking of $C_9$ and $C_{13}$ carboxylic acids back to pivalic acid offers a route to higher production of pivalic acid. In the alternative, if boron trifluoride dimethanol catalyst is used, the $C_9$ and $C_{13}$ carboxylic acids are cracked back to methyl pivalate (methyl 2,2-dimethylpropanate). Also, dependent upon market demand, this improvement offers the neoacid plant the added flexibility of tailoring the selectivity of carboxylic acid products to mostly $C_5$ or to a mixture of $C_5$, $C_9$ and $C_{13}$ acids. Pivalic acid and/or methyl pivalate are normally upgrade products versus the higher oligomers. Therefore, the present process accomplishes the goal of providing a process for high yield of pivalic acid or methyl pivalate.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A method for the production of pivalic acid comprising:

a. reacting an oligomeric neo-carboxylic acid comprising at least some $C_{13}$ carboxylic acid with a source of carbon monoxide at a temperature of less than about 200° C. in the presence of a catalyst to produce a $C_5$ carbocation product; and b. reacting said $C_5$ carbocation product with water; thereby producing pivalic acid from at least a portion of said $C_{13}$ carboxylic acid and from other neo-carboxylic acid components of the oligomeric neo-carboxylic acid.

2. The method of claim 1, wherein said oligomeric neo-carboxylic acid further comprises a $C_9$ carboxylic acid.

3. The method of claim 1, wherein said source of carbon monoxide is carbon monoxide or formic acid.

4. The method of claim 1, wherein step (a) comprises the steps of: (i) decarbonylating said neo-carboxylic acid to form a $C_{n-1}$ carbocation, wherein n is equal to the number of carbon atoms present in said neo-carboxylic acid; (ii) cracking said $C_{n-1}$ carbocation to form a $C_4$ carbocation; and (iii) reacting said $C_4$ carbocation with said source of carbon monoxide to form said $C_5$ carbocation product.

5. The method of claim 1, wherein said temperature of step (a) is from about 90° C. to about 200° C.

6. The method of claim 5, wherein said temperature of step (a) is from about 90° C. to about 150° C.

7. The method of claim 1, wherein the partial pressure of carbon monoxide is from about 50 psig to about 2000 psig.

8. The method of claim 7, wherein said partial pressure of carbon monoxide is from about 500 psig to about 1500 psig.

9. The method of claim 1, wherein the molar ratio of catalyst to oligomeric neo-carboxylic acid is at least 1:1 .

10. The method of claim 1, wherein said catalyst is at least one selected from the group consisting of hydrates of boron trifluoride, hydrofluoric acid, sulfuric acid, solid acid catalysts, and mixtures thereof.

11. The method of claim 10, wherein said catalyst is a boron trifluoride dihydrate.

12. The method of claim 11, wherein said water in step (b) comprises water obtained from the boron trifluoride dihydrate and additional water is used to regenerate said boron trifluoride dihydrate.

13. The method of claim 12, wherein the molar ratio of said water used to regenerate said boron trifluoride dihydrate to said oligomeric neo-carboxylic acid is at least about 1:1.

14. A method for production of pivaic acid comprising:
   a. reacting isobutylene, carbon monoxide, and a first catalyst to produce a reaction mixture;
   b. contacting said reaction mixture with water, thereby producing a crude acid product comprising pivalic acid and oligomeric neo-carboxylic acid;
   c. then separating said pivalic acid and said oligomeric neo-carboxylic acid from said crude acid product;
   d. then reacting said oligomeric neo-carboxylic acid with a source of carbon monoxide at a temperature of less than 200° C. in the presence of a second catalyst to produce a $C_5$ carbocation product, wherein said first and second catalysts are either the same or different; and
   e. reacting said $C_5$ carbocation product with water; thereby producing pivalic acid having an overall yield of at least 80 wt. %.

15. The method of claim 14, wherein step (d) comprises the steps of: (i) decarbonylating said neo-carboxylic acid to form a $C_{n-1}$ carbocation, wherein n is equal to the number of carbon atoms present in said neo-carboxylic acid; (ii) cracking said $C_{n-1}$ carbocation to form a $C_4$ carbocation; and (iii) reacting said $C_4$ carbocation with said source of carbon monoxide to form said $C_5$ carbocation product.

16. The method of claim 14, wherein the temperature during step (d) is from about 90° C. to about 200° C.

17. The method of claim 14, wherein said partial pressure of carbon monoxide in step (d) is from about 50 psig to about 2000 psig.

18. The method of claim 17, wherein said partial pressure of carbon monoxide in step (d) is from about 500 psig to about 1500 psig.

* * * * *